United States Patent
Steinert

Patent Number: 6,019,755
Date of Patent: *Feb. 1, 2000

[54] EPITHELIUM REMOVAL

[76] Inventor: Roger F. Steinert, 83 Sandra La., North Andover, Mass. 01845

[*] Notice: This patent is subject to a terminal disclaimer.

[21] Appl. No.: 08/927,862

[22] Filed: Sep. 11, 1997

Related U.S. Application Data

[63] Continuation of application No. 08/567,896, Dec. 6, 1995, abandoned, which is a continuation of application No. 08/218,720, Mar. 28, 1994, Pat. No. 5,505,724.

[51] Int. Cl.⁷ .................................................. A61B 17/36
[52] U.S. Cl. .................................................. 606/5; 606/12
[58] Field of Search ................................ 606/4, 5, 6, 10, 606/11, 12

[56] References Cited

U.S. PATENT DOCUMENTS

| | | | |
|---|---|---|---|
| 4,941,093 | 7/1990 | Marshall et al. | |
| 4,994,058 | 2/1991 | Raven et al. | 606/5 |
| 5,123,902 | 6/1992 | Müller et al. | 606/21 |
| 5,279,298 | 1/1994 | Flower | 606/4 |
| 5,279,611 | 1/1994 | McDonnell | 606/4 |
| 5,356,409 | 10/1994 | Nizzola | 606/5 |
| 5,376,086 | 12/1994 | Khoobehi et al. | 606/4 |
| 5,395,356 | 3/1995 | King et al. | 606/11 |
| 5,480,396 | 1/1996 | Simon et al. | 606/4 |
| 5,505,723 | 4/1996 | Muller | 606/5 |
| 5,505,724 | 4/1996 | Steinert | 606/5 |
| 5,549,599 | 8/1996 | Sumiya | 606/10 |
| 5,603,709 | 2/1997 | Johnson | 606/5 |
| 5,613,965 | 3/1997 | Muller | 606/5 |
| 5,634,920 | 6/1997 | Hohla | 606/12 |

FOREIGN PATENT DOCUMENTS

WO 94/07447  4/1994  WIPO.

OTHER PUBLICATIONS

Investigative Opthalmology and Visual Science, vol. 31 #4 (Supp) 1990; 477, including No. 2340–4, Quantification of the Fluorescence Spectra Produced by ArF Laser Ablation of the Cornea and Sclera, by Tuft et al.

Primary Examiner—Linda C. M. Dvorak
Assistant Examiner—Sonya C. Harris
Attorney, Agent, or Firm—Hale and Dorr LLP

[57] ABSTRACT

Accurate, non-mechanical removal of the epithelium from essentially only the area of the cornea to be treated. In particular, an epithelium-ablative laser device irradiates the selected region of the epithelium with ablative laser energy, a spectroscopic system monitors the ablation and spectroscopically determines whether epithelium is being ablated, and a control system terminates the epithelium removal upon spectroscopic determination of a substantial absence of epithelium ablation.

13 Claims, 2 Drawing Sheets

EPITHELIUM REMOVAL

This application is a continuation of application Ser. No. 08/567,896, filed Dec. 6, 1995, now abandoned, which is a continuation of application Ser. No. 08/218,720, filed Mar. 28, 1994, now U.S. Pat. No. 5,505,724.

FIELD OF INVENTION

This invention relates to treatment of the eye and, more particularly, to a system and method for controlled removal of the epithelium of the cornea.

BACKGROUND OF INVENTION

Photorefractive keratectomy is a procedure in which excimer lasers are used to correct optical errors of the eye, such as myopia, near-sightedness, hyperopia, far-sightedness and astigmatism. One typical procedure is to remove corneal tissue using a laser configured at 193 nanometers, although other wavelengths may also be used. Each pulse of the laser removes a small amount of corneal tissue and, by controlling the number of pulses and exposure pattern of the laser, the cornea can be reshaped as desired. For example, to correct near-sightedness, more tissue is removed from the center than at the edge, so that there is an overall flattening of the cornea.

An initial step in the procedure is to remove from the cornea the surface layer of cells known as the epithelium. The epithelium, typically about fifty microns thick, covers and protects the underlying tissue, principally collagen, that makes up the bulk of the cornea. In the past, the epithelium has been removed by scraping with a mechanical device, such as the edge of a blade or other surgical instrument. This has a number of disadvantages.

For example, the use of any mechanical instrument presents some risk of infection, and mechanical removal is also inherently irregular and highly dependent on the skill of the person accomplishing the procedure. Scraping may injure the underlying cornea, e.g., by causing nicks or scratches which may in turn affect the smoothness of the later removal of the underlying collagen, and small "islands" of epithelium may remain after it is thought that all the epithelium has been removed or, in the course of scraping away the epithelium, some of the underlying collagen may be removed also. Moreover, to assure that the entire area to be treated has been exposed, it is usually necessary to remove the epithelium from an area that is larger than that to be treated. This is undesirable since, among other things, a larger area requires longer to heal and results in an increased risk of infection. For example, if the area of the collagen 16 to be treated is 5 millimeters in diameter, using mechanical ablation techniques it is usually necessary to remove the overlying epithelium 14 from a 6 or even a 7 millimeter zone. This result is that the overall exposed area is between about one and a half and two times the size of the treatment zone. Further, if the epithelium is mechanically removed, the laser used to ablate the underlying collagen cannot be positioned until after the epithelium removal has been completed, and this undesirably increases potential dehydration and the overall length of the surgical procedure.

SUMMARY OF INVENTION

The present invention provides for accurate, non-mechanical removal of the epithelium from essentially only the area of the cornea to be treated. In particular, an epithelium-ablative laser device irradiates the selected region of the epithelium with ablative laser energy, a spectroscopic system monitors the ablation and spectroscopically determines whether epithelium is being ablated, and a control system terminates the epithelium removal upon spectroscopic determination of a substantial absence of epithelium ablation.

In preferred embodiments in which the same laser device is then used to reshape the exposed cornea after the covering epithelium has been removed, the spectroscopic system detects characteristic fluorescence from corneal epithelium being ablated, the laser delivers energy in pulses, and the spectroscopic system examines for presence of epithelium fluorescence between pulses.

DETAILED DESCRIPTION OF PREFERRED EMBODIMENTS

Figure 1:
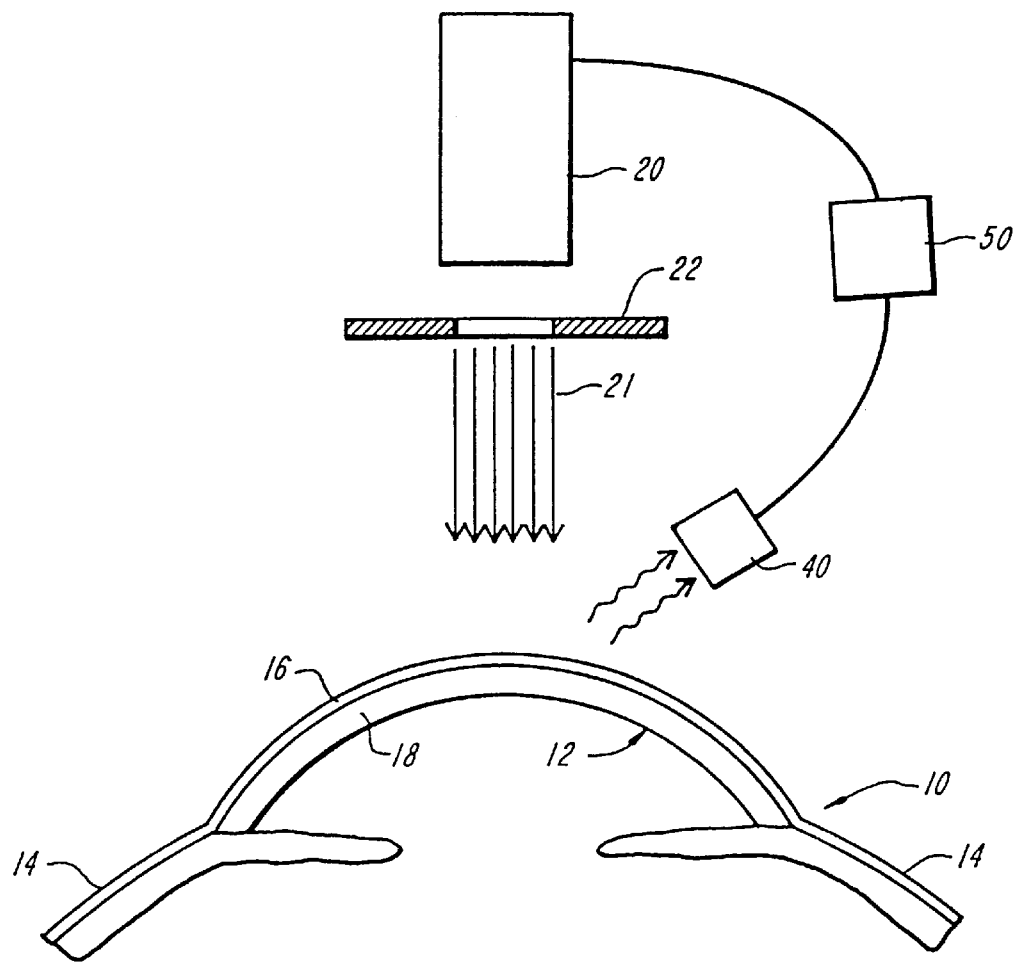
FIG. 1 is a schematic illustrating a system according to the present invention.
Figure 2:
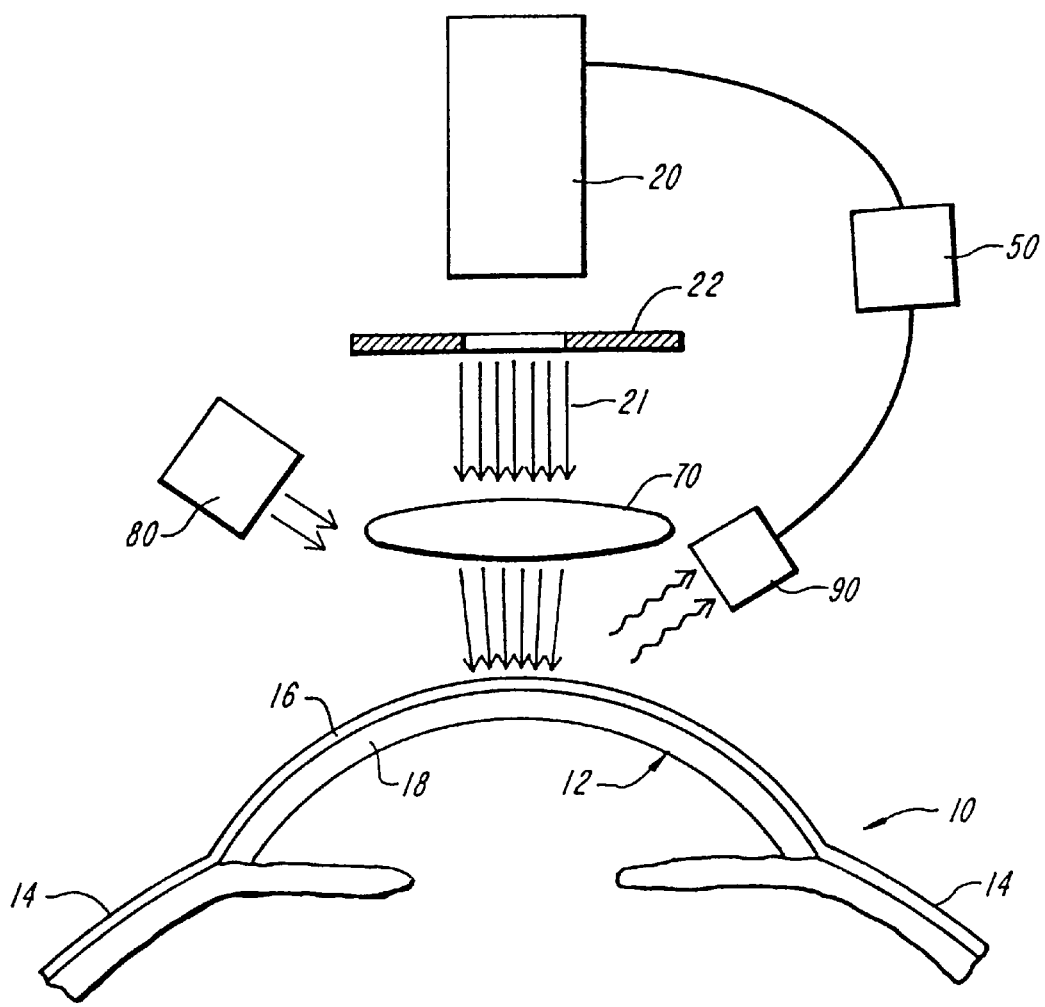
FIG. 2 is a schematic illustrating a modified system also embodying the invention.

FIGS. 1 and 2 show a portion of a human eye, generally designated 10. As is well known, the cornea 12, surrounded by the sclera 14, includes an outer epithelial layer 16 (the epithelium) overlying the tissue 18 (largely collagen) that forms the bulk of the corneal structure. The epithelium 16 is typically about 50 microns thick, but the thickness varies from person to person. For example, the epithelium of a contact lens wearer is often only about 60% as thick as that of a typical person who does not wear contact lenses.

FIGS. 1 and 2 also show an excimer laser 20, e.g., an Omnimed II manufactured and sold by Summit Technology, Inc. of Waltham, Mass. Laser 20 emits a beam 21 of pulsed laser energy at a wavelength of about 193 nanometers, and is conventionally used to reshape the collagen 18 forming the corneal lens by selective ablation of the collagen tissue after the protective epithelium layer 16 has been mechanically removed. A variable aperture diaphragm 22 is provided in the beam path to control, and as necessary to vary, the diameter of the laser beam 21. As conventionally used, the aperture is set so that the diameter of the beam incident on the cornea is equal to that of the area to be treated. When different corneal thicknesses are to be removed from different areas, a smaller aperture may be employed and only a small amount of the overall treatment area ablated at any particular time. In either event, each pulse of the excimer laser ablates a small amount of corneal collagen tissue.

It has been found that the laser ablation of the corneal collagen tissue causes emitted fluorescence. See Tuft et al., "Qualification of the Fluorescence Spectra Produced by ArF Laser Ablation of the Cornea and Sclera," *Investigative Opthalmology and Visual Science*, Vol. 31 No. 4 (Supp.) 1990, 477. Typically, the fluorescence caused by each ablating laser pulse follows, and exists for a period of time considerably shorter than the width of, the laser pulse itself. Tuft et al. found that the fluorescence resulting from a pulsed ArF laser had a duration on the order of 1–3 nanoseconds, about an order of magnitude less than the laser pulse width.

It has been found that the laser beam from an excimer laser may also be used to ablate or remove the epithelial layer overlying the collagen structure of the cornea, but this has been proved difficult for a number of reasons. The thickness of the epithelium is difficult to measure accurately and, as has already been noted that the thickness of the epithelium varies from person to person. Additionally, the cellular structures of the epithelium and underlying collagen are sufficient different that the two ablate at different rates. Accordingly, although the laser will ablate the epithelium as well as the collagen tissue, it is not practical simply to use the laser to start ablation at the outer surface of the epithelium 16, and then to work down into the underlying collagen tissue 18. Rather, it is important to know when the covering epithelium has been completely removed, and only then to begin removal of the underlying collagen. If the point at which collagen tissue commences is not precisely known, it is difficult, if not effectively impossible, to have control collagen removal as is necessary for accurate corneal reshaping.

It also has been found that, because of their different cellular structures, the collagen and overlying epithelium have significantly different spectroscopic characteristics, and that these spectroscopic differences may be used to provide an accurate measure of epithelium removal.

For example, the fluorescence caused by excimer laser ablation of the epithelium 16 differs from produced by ablation of the underlying collagen 18. The fluorescence from the collagen tissue is a mixture of wavelengths, peaking at about 300 nanometers, in the ultraviolet range. Ablation of the epithelium also produces a range of fluorescence, but the peak is in the barely visible blue range, e.g., is in the range of about 400 nanometers. Both wavelengths can be detected using a conventional diode array detector such as that employed by Tuft; and the type of cells being ablated by the laser (e.g., epithelial cells or collagen cells) can be determined by monitoring the presence or absence of a fluorescence peak at the corresponding wavelength, e.g., barely visible blue (about 400 nanometer) or ultraviolet (about 300 nanometer). Since fluorescence from the abraded epithelium is visible to the human eye and vanishes when epithelium removal has been completed, it is also possible to monitor epithelial ablation visually.

Thus, according to one aspect of the present invention, a photodiode (designated 40 in FIG. 1) sensitive to the characteristic peak of either collagen or epithelium ablative fluorescence is used to determine which of the two types of cells is being ablated. Preferably, the photodiode 40 is sensitive to epithelium-caused fluorescence (e.g., to fluorescence in the about 400 nanometer wavelength range, and the presence or absence of such a fluorescence peak is used as a control signal. Fluorescence having such a peak will be present so long as the laser is removing epithelium. Once the epithelium has been removed, that peak drops significantly. Control system 50, connected to both laser 20 and photodiode 40, is responsive to the photodiode 40 and either causes the lasing action of the laser to stop (as in the illustrated embodiment) or automatically causes the control system to commence the corneal-reshaping.

Preferable, the same laser source and beam are used for both epithelium removal and subsequent reshaping of the underlying corneal tissue. As will be evident, this substantially avoids the previously significant difficulty of insuring that the laser is properly registered relative to the exposed area. It will also be noted that the width of the beam used for epithelium removal is same as the maximum laser beam diameter to be used for subsequent corneal reshaping, i.e., the laser is used first to remove the epithelium from the entire area to be treated, and then to provide the collagen ablation required for reshaping. If a smaller diameter laser beam is used for reshaping, e.g., because different thicknesses are to be removed from different sub-areas of the entire treatment area, it will be seen that the epithelium bordering the complete treatment area acts as a protective mask.

In the embodiment of FIG. 1, it will be seen that the laser beam 21 is substantially perpendicular to the entire portion of the eye being treated. The diameter of the treated portion, e.g., about 5 mm, is sufficiently small that the laser beam is substantially normal to all portions of the eye being treated. If a larger, e.g., 8–9 mm diameter, area is to be treated, the curvature of the eye may become significant. In such circumstances, although the radiation from the laser 20 is emitted as parallel rays, they will impinge on the eye at different angles and may cause ablation of epithelium at different rates in different areas. Accordingly, it may be to provide additional means to insure ablation of epithelium throughout the selected region is substantially the same.

FIG. 2 shows a lens 70 placed between the laser and eye. Although the laser beam 21 is emitted from laser 20 as parallel rays, the optical characteristics of the lens 70 are such that, after passing through the lens, the laser beam rays are slightly convergent so that, throughout the treatment area, each ray is incident on the eye at a substantially normal angle.

Alternatively, an ablative mask of varying thickness may be provided between the laser source and the eye surface. The various portions of the mask block the laser beam until the particular mask portion has been ablated, and thus make it possible to vary the period of time during which the laser is incident on different areas of the epithelium and thus assure equal thickness of epithelium ablation over the entire treatment area.

Whatever the circumstances, the system determines when all the epithelium has been removed, and the transition into the underlying collagen has begun, by sensing a spectroscopic difference between the epithelial and collagenic tissue.

Other Embodiments

In other embodiments, other spectral characteristics of the epithelium may be employed to provide a control signal indicative of the fact that the epithelium overlying the treatment area, but little or none of the underlying tissue, has been removed. For example, either reflective or transmissive spectroscopy may be employed. FIG. 2 illustrates a light source 80 incident on the treatment area, and a sensor 90 (rather than a photodiode as in FIG. 1) that is responsive to the reflected light from the source. Since, as is well known, the characteristics of the reflected light depend on the cellular structure of the surface on which light from the source is incident (and from which it is reflected), sensor 90 provides a control signal indicating that the reflected light is from a collagen tissue surface (or, alternatively, is not from epithelium tissue), and that substantially all of the epithelium has been removed.

Regardless of the particular spectroscopic methodology employed, the transition between epithelium and collagen removal is indicated with considerably more accuracy than heretofore possible, and the size and thickness of any residual "islands" of epithelial material are substantially reduced.

These and other embodiments will be within the scope of the following claims.

What is claimed is:

1. A system for controlled removal of epithelium from a selected region of a cornea, said system comprising:

an epithelium-ablative laser device for directing ablative irradiation onto a selected region of the epithelium to ablate said region and cause fluorescence from said region, a spectroscopic system arranged to spectroscopically monitor the selected region during the application of irradiation from said laser device onto said region and including a detector for detecting fluoresence from said region that is characteristic of fluorescence caused by irradiation of epithelium and a control system connected to the laser device and responsive to the spectroscopic system for terminating application of radiation from said laser device to said region upon detection by said detector of substantial absence of said characteristic fluorescence.

2. The system of claim 1 wherein said spectroscopic system is responsive to the detection by said detector of a deep blue fluorescence characteristic of corneal epithelium being ablated and said control system is responsive to said detector to cause application of said ablative radiation from said laser device to said region to cease upon detection by said detector of the absence of said deep blue fluorescence.

3. The system of claim 2 wherein said laser device emits laser energy at a wavelength of about 193 nm.

4. The system of claim 1 wherein said epithelium-ablative laser device emits laser energy at a wavelength to ablate collagen for reshaping the cornea.

5. The system of claim 4 wherein the laser device emits a beam of laser energy and includes a variable aperture for controlling the diameter of said beam over the duration of exposure for effecting a preselected refractive correction.

6. The system of claim 1 wherein said laser device is an excimer laser.

7. The system of claim 1 in which said epithelium-ablative laser device is arranged to deliver at least most of said ablative irradiation in pulses, and said spectroscopic system is operative to monitor the selected region and detect said fluorescence between said pulses.

8. The system of claim 1 in which radiation from said laser device is emitted as parallel rays, and means are provided to cause the rays distributed over a range of curvature in the selected region to have substantially the same ablation of epithelium thickness.

9. The system of claim 8 including means for varying energy deposited over said selected area to assure equal thickness of epithelium ablation over said area.

10. The system of claim 1 wherein said laser device emits radiation as parallel rays, and wherein said system includes means to cause the rays to have substantially a normal angle of incidence over the selected region of epithelium.

11. The system of claim 10 in which said means comprises a lens system.

12. A system for controlled removal of epithelium from a selected region of a cornea, said system comprising:

an epithelium-ablative laser device for emitting ablative irradiation as parallel rays, directing said rays onto a selected region of the epithelium to ablate the region, and distributing the rays over a range of curvature in the selected region to have substantially the same ablation of epithelium thickness.

a spectroscopic system arranged to spectroscopically monitor the selected region during application of irradiation from said laser device onto said region and including a detector for detecting fluorescence from said region that is characteristic of fluorescence caused by irradiation of epithelium, a control system connected to the laser device and responsive to the spectroscopic system for terminating application of radiation from said laser device to said region upon detection by said detector of substantial absence of the epithelium, and an erodible ablative mask positioned between the laser device and the selected region in the path of ablative irradiation from said laser device to said region.

13. A system for controlled removal of epithelium from a selected region of a cornea, said system comprising:

an epithelium-ablative laser device for directing ablative irradiation onto a selected region of the epithelium to ablate the region, a spectroscopic system arranged to spectroscopically monitor the selected region during application of irradiation from said laser device onto said region and including a detector for detecting fluorescence from said region that is characteristic of fluorescence caused by irradiation of epithelium, a control system connected to the laser device and responsive to the spectroscopic system for terminating application of radiation from said laser device to said region upon detection by said detector of substantial absence of the epithelium, and an erodible ablative mask positioned between the laser device and the selected region in the path of ablative irradiation from said laser device to said region.

* * * * *